(12) United States Patent  
Binder

(10) Patent No.: US 6,607,537 B1
(45) Date of Patent: Aug. 19, 2003

(54) INJECTOR FOR IMPLANTING A FOLDED INTRAOCULAR LENS, CONTAINER FOR STORING AND TRANSPORTING THE INJECTOR AND METHOD FOR EJECTING THE LENS IN A FOLDED STATE

(76) Inventor: Helmut Binder, Reinganumstrasse 12, Frankfurt am Main (DE), D-60385

( * ) Notice: Subject to any disclaimer, the term of this patent is extended or adjusted under 35 U.S.C. 154(b) by 0 days.

(21) Appl. No.: 09/890,756
(22) PCT Filed: Feb. 1, 2000
(86) PCT No.: PCT/DE00/00262
§ 371 (c)(1),
(2), (4) Date: Aug. 3, 2001
(87) PCT Pub. No.: WO00/45746
PCT Pub. Date: Aug. 10, 2000

(30) Foreign Application Priority Data

Feb. 3, 1999 (DE) .......................... 199 04 220

(51) Int. Cl.[7] ................................. H61F 9/00
(52) U.S. Cl. ...................................... 606/107
(58) Field of Search .................... 606/107; 623/6.12

(56) References Cited

U.S. PATENT DOCUMENTS

| 5,123,905 A | 6/1992 | Kelman |
| 5,139,501 A | 8/1992 | Klaas |
| 5,190,552 A | 3/1993 | Kelman |
| 5,190,553 A | 3/1993 | Kanert et al. |
| 5,468,246 A | 11/1995 | Blake |
| 6,497,708 B1 * | 12/2002 | Cumming .................. 606/107 |

FOREIGN PATENT DOCUMENTS

| DE | 40 39 119 | 9/1991 |
| DE | 41 10 278 | 10/1992 |
| DE | 43 03 051 | 8/1993 |
| DE | 43 01 573 | 7/1994 |
| DE | 36 10 925 | 11/1994 |
| EP | 270 257 | 6/1988 |
| EP | 340 698 | 11/1989 |
| EP | 363 213 | 4/1990 |
| EP | 402 138 | 12/1990 |
| EP | 477 466 | 4/1992 |
| EP | 497 505 | 8/1992 |
| EP | 503 136 | 9/1992 |
| WO | WO 94/10912 | 5/1994 |
| WO | WO 95/07059 | 3/1995 |
| WO | WO 95/13022 | 5/1995 |
| WO | WO 96/15743 | 5/1996 |
| WO | WO 97/13476 | 4/1997 |
| WO | WO 97/15253 | 5/1997 |
| WO | WO 98/05281 | 2/1998 |
| WO | WO 98/25548 | 6/1998 |

* cited by examiner

Primary Examiner—Eduardo C. Robert
(74) Attorney, Agent, or Firm—Ostrolenk, Faber, Gerb & Siffen, LLP

(57) ABSTRACT

An injector for implanting a folded intraocular lens with which a folded lens can be inserted into the capsule of the lens of the eye through an opening incision of about 3 mm in the eye. The injector consists of three parts, namely a one-piece body, a pivoting flap which is provided with a folding rib and by which the lens is held in an unfolded state in a first position above the transporting channel and is slid folded into the transporting channel by radial pressure, and a third component, the slider through which the folded lens can be slid forwards in the longitudinal direction and out of the injector into the eye.

13 Claims, 3 Drawing Sheets

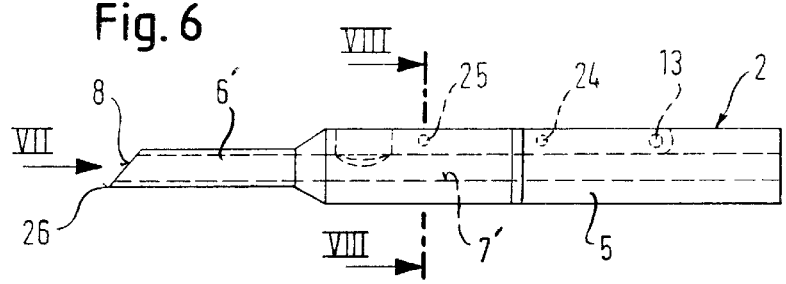
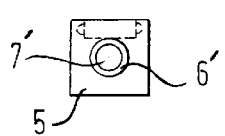 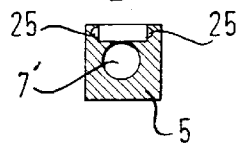
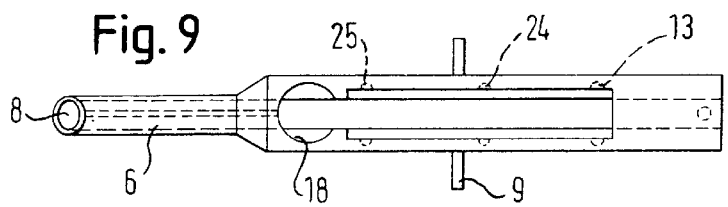
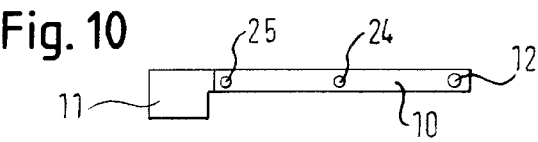
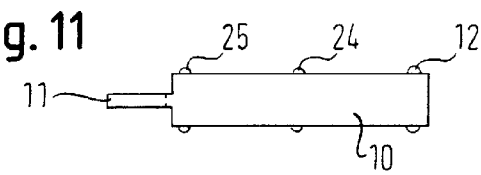
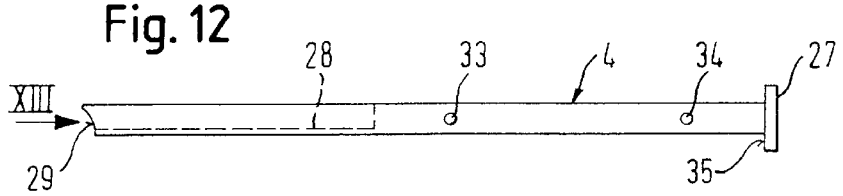
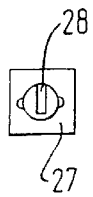
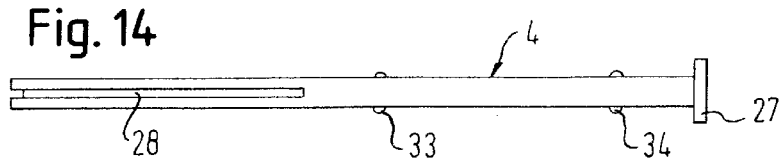

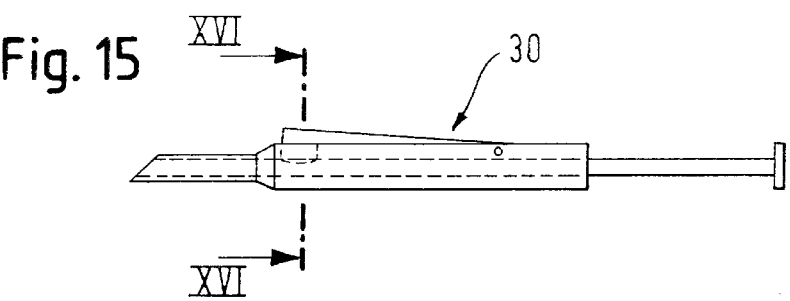
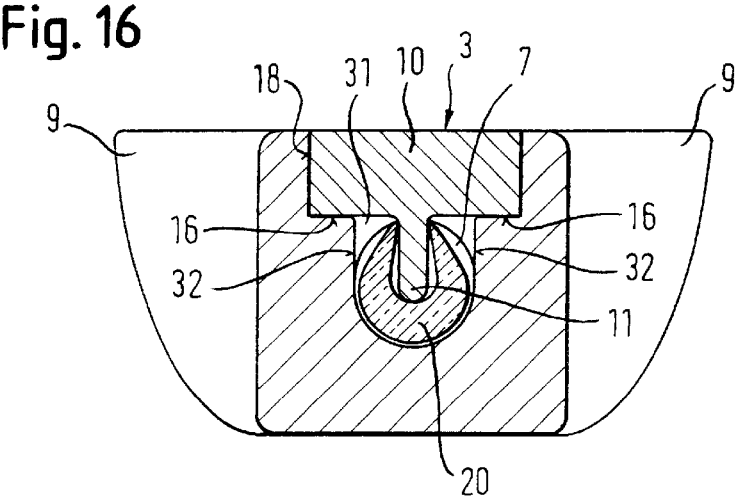
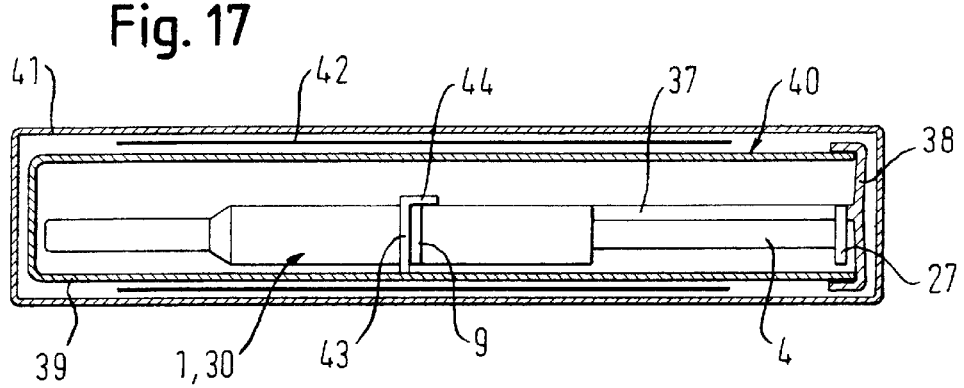
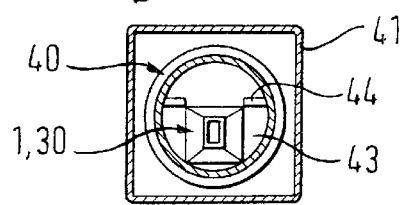

INJECTOR FOR IMPLANTING A FOLDED INTRAOCULAR LENS, CONTAINER FOR STORING AND TRANSPORTING THE INJECTOR AND METHOD FOR EJECTING THE LENS IN A FOLDED STATE

PRIORITY CLAIM

This is a U.S. national stage of application No. PCT/DE00/00262, filed on Feb. 1, 2000. Priority is claimed on that application and on the following application:
Country: Germany, Application No.: 199 04 220.9, Filed: Feb. 3, 1999.

BACKGROUND OF THE INVENTION

The invention relates to an injector for implanting a (temporarily) folded intraocular lens, with which the folded lens can be inserted in the capsula of the lens of the eye through an opening incision of approx. 3 mm in the eye.

In eye surgery it is very important that the surgical incision through which a cataract is removed and then the required artificial lens is implanted is as small as possible (approx. 3 mm) so that optimum healing is guaranteed and no suture is required. To be able to implant artificial lenses with the required diameter of approx. 5–6 mm, these must be foldable so that they pass through the small incision of 3 mm.

A wide variety of devices are known for folding the lenses and inserting the folded lens with the aid of forceps and also injectors for direct insertion of the lenses in the eye. In the case of the latter, generally the lens which is inserted essentially unfolded is progressively folded axially as it is slid forwards in the injector, or an already folded lens is inserted and only slid out.

Thus, EP 0 503 136 A1, EP 0 497 505 A1, EP 0 402 138 A1, WO 98/25548, WO 94/10912 and DE 40 39 119 C1 for example disclose devices for folding an intraocular lens in a wide variety of embodiments through which the lenses are in each case accordingly folded or prefolded and then inserted in the eye by means of forceps or an injector. This procedure is relatively complex and in addition uncertain due to the handling with the forceps as the folded lens can easily slip out of the forceps.

DE 41 10 278 A1, DE 36 10 925 C2, WO 96/15743, EP 0 270 257 A1, EP 0 477 466 A1, WO 97/113476 and WO 97/15253 disclose lens injectors in which partly prefolded lenses are inserted in the receiving chamber of an inserting cartridge which can be fastened to the front end of the injector. Usually, this cartridge also serves as receiving chamber for safely storing and transporting the lens. After the cartridge is fitted to the handle part of the injector body, the lens is slid through the tapering channel to the outlet end by axial displacement by means of a plunger, through which the lens is folded or folded again. These known injectors are of relatively complex design comprising a large number of individual parts, and the user must assemble at least two separate parts before the lens can be slid out.

WO 97/13476 discloses an injector in which the lens is first folded in a folding instrument and then placed together with the latter radially in the injector. Then, with the aid of a plunger, the folded lens is slid out of the folding device through the tapering delivery cover, through which the lens undergoes further folding. Thus, two instruments are needed here, one for the preliminary folding and one for injecting the folded lens.

WO 98/05281 discloses an injector the lens-holding cartridge of which exhibits at its rearward end a radially swivelling flap with a central holding rib by means of which the unfolded lens is pressed radially into the transporting channel and held there. However, genuine folding of the lens only takes place through the forward sliding movement of the lens through the tapering transporting channel. Thus, this is a relatively complex design with correspondingly complex handling.

In addition, WO 95/07059 and WO 95/13022 describe an injector with a cylindrical transporting channel into which an unfolded lens is slid tangentially with the aid of an independent slider rib not connected to the injector body so that the lens is rolled in the transporting channel. The rolled lens is then slid out by means of an additionally separate cylindrical slider filling the transporting channel completely. Thus, two separate parts have to be introduced into the injector and the lens delivered in a rolled state.

In addition, U.S. Pat. No. 3,123,905 A describes an injector with a cylindrical body and a cylindrical transporting channel which is provided coaxially therein and debouches into a delivery tip which tapers conically. The cylindrical injector body incorporates a relatively narrow radial insertion slot through which the lens placed on the surface of the body over the insertion slot is pressed in with the aid of an independent insertion rib. Apart from the fact that this known injector cannot be used at the same time for transporting and safely storing an unfolded lens, the insertion of the lenses through the very narrow insertion slot is difficult or even impossible since lenses are known to be practically incompressible. In addition, the independent rigid slider also fills the entire cross-section of the transporting channel so that the insertion rib must be removed after insertion of the lens. In addition, the transporting channel tapers conically to a point so that the inserted lens, in cylindrical form in the channel, is rolled up even further when it is slid out, giving major delivery problems.

Lastly, DE 43 03 051 A1 and U.S. Pat. No. 5,190,552 A show an injector in which an unfolded lens is inserted through a radial insertion opening into the transporting channel which is open upwards radially in this section, on to a lens-holding slide. The lens is held securely to prevent it dropping out by means of a lens locking rod which is slid axially over the inserted lens. When slid out, the holding rod and the slide are together slid through an at least initially tapering transporting channel of the injection tube, through which the lens, still held centrally by the holding rod, is folded around this rod. This is also a relatively complex design with relatively complex handling. In addition, the lens must be held securely pressed down in its position in the slide by the locking rod as it is slid forwards so as not to be slid off the slide by the rod.

SUMMARY OF THE INVENTION

The object of the invention is to provide an injector of the kind named above which exhibits the simplest possible construction and allows reliable sterile handling during safe storage, transport, folding and implanting of the lenses.

According to the invention, the transporting channel of the one-piece injector body is an axially continuous opening with a constant cross-section. Thus, the transporting channel has a cross-section which is always the same throughout the entire injector, namely from the slider inlet end to the lens delivery end, which represents a simplification in terms of manufacturing. In addition, the supporting surface for the unfolded lens is arranged radially offset upwards in the direction of insertion relative to the transporting channel. As a result of this, the lens is inserted lying above the transporting channel or at least essentially a distance from the bottom of the transporting channel, but at the same time below the upper surface of the body. Lastly, the holding rib or rod holding the unfolded lens on the supporting surface is a radially extending plate-shaped folding rib which is arranged like the die of a stamping tool and can be pressed radially well into the transporting channel or transversely to the transporting direction through the slot-shaped insertion opening. Thus, the folding rib and the body act like a correspondingly embodied mold and die on the lens lying between them and bend this in the middle, at the same time sliding it into the transporting channel in its final folded state. Then, it is only necessary for the lens to be slid forwards in this final folded state in the transporting channel by the slider, which here obviously is also a rod with a constant cross-section.

In a further embodiment of the invention, the one-piece injector body can exhibit a rectangular cross-section overall, i.e. both the thicker insertion and folding part and the thinner injecting part and the transporting channel each exhibit a rectangular cross-section. All these parts, namely the body sections and the transporting channel, can also exhibit a round or oval cross-section or the holding part can be rectangular while the injection tube and the transporting channel exhibit a round cross-section.

Obviously, in its cross-section the transporting channel has to be embodied according to the dimensions of the folded lens. Thus, the width of the channel must be roughly equal to double the thickness of the lens plus the thickness of the folding rib, while the height of the channel should be at least equal to half the diameter of the lens. In addition, it its width in relation to the surfaces surrounding it such as the walls of the transporting channel, the folding rib is embodied so that the cilia of the lens are not jammed and damaged during folding and displacement.

Since the dimensions of the injector are relatively small overall, its components are made so that they partly engage in one another in operation, which is possible through the maximum simplification of the components. After the lens is folded by pressing the folding rib into the transporting channel, the folding rib in fact also remains pressed in, preferably detained, while the folded lens is slid out. Therefore, on its upper side the sliding rod with the constant cross-section exhibits a longitudinal groove which embraces the folding rib in a U-shape with a small sliding tolerance during the longitudinal movement. In addition, it is advantageous when the front side of the slider is embodied matching the shape of the folded lens, i.e. with an inward curve over approximately a quarter cylinder, so that a uniform sliding pressure is exerted on the lens.

To guarantee reliable handling of the injector in its roles as a lens-holding, lens-folding and lens-inserting device, detent and indexing means are provided on the slider, folding flap and body for the four different working end positions.

Thus, three positions are provided for the slider, with corresponding positioning means, namely a first position for determining the slider positions in the position retracted behind the radial insertion opening, a second advanced position in which the folded lens is slid close to the front delivery opening of the injection tube, and lastly a third and final position in which the end face of the slider reaches the outlet opening of the injection tube. The first two positions can be achieved through indexing balls or projections or similar means, while the third position can also be achieved through abutment of the thrust plate provided on the injector body at the outer end of the slider projecting from the injector body.

According to the invention, the preferably round supporting surface for the unfolded lens is divided by the insertion and folding slot into two part surfaces which are aligned horizontally, i.e. parallel to the bottom of the transporting channel and at the same time to the upper side of the injector body. However, these part supporting surfaces can also be aligned inclined inwards in the direction of the transporting channel in the shape of a roof (i.e., V-shaped), preferably at an angle of 30° to the horizontal or to the upper side of the body, or inclined at an angle roughly corresponding to the inclination of the lens body. This and additional large transitional radii between the supporting surface parts and the folding slot allow an optimum folding movement.

It is advantageous when longitudinal narrow supporting strips are provided just above the supporting surface, by means of which the lens is placed on the supporting surface under slight tension and which at the same time serve as supporting strips for the stop strips provided on the folding rib or on the corresponding pivoting lever. Thus, these supporting strips also ensure that the lenses are at least held gently.

The folding rib pivotable radially into and out of the transporting channel through the insertion opening is provided at the front end of a pivoting lever articulated pivotably on the upper side of the body. In this case, the upper side of the body holding part can be provided with a correspondingly wide groove in which the pivoting lever is inserted completely without projecting from the surface when pivoted or swung in. However, to allow the pivoting lever to be swung out again, it must be possible to grasp the inserted lever, for example by means of a thrust plate which is provided on the lever over the folding rib and which extends over the entire width of the body, or by other means. However, the lever can also be articulated by means of appropriate pivot lugs on the body so that it lies flat on the body. In this case, these pivot lugs on the body can be opened upwards by means of a narrow slot in a manner known per se, so that the pivot pins can be pressed into the mounting openings by means of these slots. However, such a hinge snap assembly can also be provided in the embodiment of the lever in which it is inserted in the body.

In order to determine the two working positions of the folding rib by means of the lever of the folding rib which can be pivoted through approx. 180°, corresponding indexing devices are provided on the lever and the body, through which in each case an angular position of the lever is determined for lying on and holding the unfolded lens and for holding the folded lens in the inserted position. This prevents the lever pivoting upwards or exerting insufficient pressure in the holding position or in the folding position with the result that the lens falls out or moves, so that its correct delivery is not assured.

According to one development of the idea of the invention, to facilitate handling and also to fix the injector in a transport container as described further on, a transversely extending grip plate is provided roughly in the middle on both sides of the body holding part. As a result of this, in particular when ultimately delivering the folded lens from the injector or placing this lens in the eye, the injector can be handled in roughly the same way as an injection syringe.

It is particularly advantageous when the injector consisting of only three parts, namely the injector body, slider and flap, is made entirely of transparent plastic, e.g. by injection molding, so that the three injector components are assembled or held together by simply pressing them into or onto one another. Apart from that, the transparent design of the injector allows precise monitoring of the position of the lens. For example it is possible to observe how the unfolded lens is lying, how this is then folded by means of the folding rib when it is pressed into the transporting channel, and then slid forwards by means of the slider and then slid out.

Any error in the positioning of the lens can then be observed at once so that the person handling the injector can adjust his further actions to this circumstance.

Obviously, the injector body can be embodied in two parts for production reasons, with a dividing plane parallel to the transporting channel. After production by injection molding for example, the two body parts are assembled and glued together.

In addition, according to the invention, the slider can be embodied in two parts, being composed of a front longitudinally displaceable part and a rearward rotatable part. The rearward part exhibits a thread which is guided in a threaded bore of the holding part in order to ensure precisely controllable forward movement of the slider and hence of the lens. In addition, retraction of the complete slider assembly can be achieved through known means, such as openings and snap pins on the adjacent end sides of the parts of the slider.

For storing and transporting an injector according to the invention, a receiving container can be used which essentially consists of a sleeve with a cover in which lateral holding plates are provided for positioning the injector by means of its lateral grip plates. The holding plates each have a barb which points in the direction of introduction, which barbs grip over the injector grip plates and hold the injector securely lying on the inner wall of the container. Optimum positioning of the injector in the container is achieved through an axial projection which is provided on the cover and extends to the rearward end face of the injector body when the cover is fitted, or through a slotted spacer tube which is fitted between the rearward end side of the injector body and the rear thrust plate of the slider and in addition through the bearing of the rearward end face of the slider thrust plate on the internal end side of the cover which can be lined with very soft elastic plastic. Thus, even with careless handling of the container, the slider cannot be unintentionally slid forwards in the transporting channel beyond its rear retracted detent position, which could lead to the unfolded lens lying on the supporting surface being pushed off and expelled or even damaged.

The transport container or at least its receiving sleeve can also be made of transparent plastic in a manner know per se, e.g. by injection molding or blow molding, so that it is easy to establish whether the injector—and the lens—are in the correct position.

The transport container with the injector located in it can be filled with a sterile transport liquid known for safe storage and delivery of folding lenses. In this case, after the introduction of the injector, the container sleeve is filled with the liquid in a vertical position with the opening uppermost. When the cover is fitted, the projection on the cover and/or the inner cover cone displace liquid so that no air remains in the closed container, guaranteeing sterile safe storage of the injector and retention of the elasticity of the lens.

As is general practice with drugs and medical instruments, the transport container for its part can be placed in a packaging carton in which a packing slip is also enclosed, guaranteeing additional protection for the transport container and the injector and ultimately the lens itself.

For folded delivery of an intraocular lens by the injector according to the invention, the pivoting lever covering the radial insertion opening in the injector body is swung back through approx. 180°, exposing the insertion opening, after which an unfolded lens is inserted and placed on the supporting surface provided at the upper end of the insertion opening. Then, the pivoting lever is swung back again through approximately 180° until the underside of its folding rib rests on the upper side of the lens body, if possible with the lever detained in this holding position. Then, in this state the "loaded" injector is used or it is inserted and fixed in a transport container and placed in a packaging carton etc. for safe storage for use later or prepared for transport to other locations for use.

When it is to be used during an implant operation, the injector is first removed from a container and the pivoting lever is pressed in radially as far as the stop, e.g. by pressing on its thrust plate with the folding rib located underneath it, so that the folding rib presses the underlying lens off the supporting surface through the folding slot into the transporting channel. At the same time, the lens lies and is folded symmetrically longitudinally elastically around the folding rib and in the process is brought into the folded insertion state. After this, the slider is slid out of its retracted resting position into the second position, through which the lens is brought to its position close to the ejection opening in the transporting channel. Thus, the injector is ready for use for implanting the folded lens located in it.

Then, after the short surgical incision has been made in the eye and the narrow injection tube part of the injector, the tip of which should be embodied so that it tapers into an extremely shallow point for easier introduction, has been introduced into the interior of the eye through the iris just above the lens sac, the injector slider is slid inwards further as far as the end stop, through which the lens is slid out of the tip of the injector into the lens sac. Then, the injector is pulled out and either discarded as a single-use part or placed in safe storage for reloading with an unfolded lens as a multiple-use part.

In the following, the invention is described in greater detail on the basis of a plurality of embodiment examples with reference to the drawing.

In this

BRIEF DESCRIPTION OF THE DRAWINGS

FIG. 6 shows a side view of an injector body in a second embodiment, with a rectangular body holding part and a round injection tube, transporting channel and slider;

FIG. 7 shows an end elevation view according to the arrow VII in FIG. 6;

FIG. 8 shows a section VIII—VIII in FIG. 6;

FIG. 9 shows a plan view of the injector body according to FIG. 6;

FIG. 10 shows a side view of a pivoting lever with folding ribs, for use in conjunction with the injector body according to FIGS. 5–8;

FIG. 11 shows a plan view of the pivoting lever according to FIG. 10;

FIG. 12 shows a side view of a slider for use in conjunction with the injector body according to FIGS. 6 to 9;

FIG. 13 shows a front view of the slider according to FIG. 12;

FIG. 14 shows a plan view of the slider according to FIGS. 12 and 13, showing the groove for sliding along the folding rib;

FIG. 15 shows a 1:1 scale side view of an injector according to FIGS. 6 to 14;

FIG. 16 shows a vertical section XVI—XVI in FIG. 15, with the pivoting lever pressed in, with a slightly modified form of lever and supporting surface;

FIG. 17 shows a longitudinal section through an injector packed in the transport container and packaging carton;

FIG. 18 shows an end elevation view with the bottom removed from the container and carton.

DETAILED DESCRIPTION OF THE PREFERRED EMBODIMENTS

Figure 1:
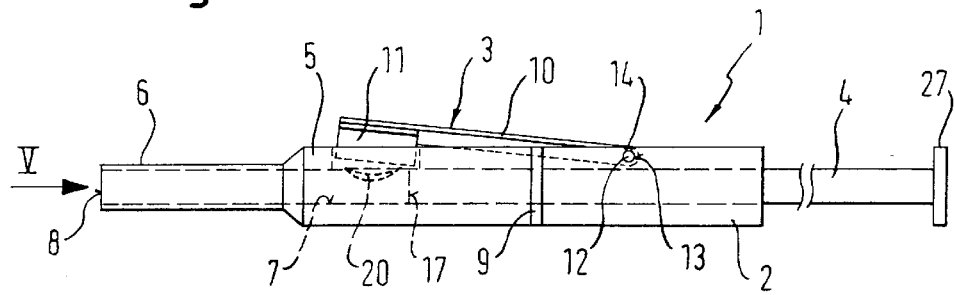
FIG. 1 shows a side view of an injector according to the invention in a first embodiment, with an unfolded lens loaded and the holding flap lying on it.

As can be seen in particular in FIG. 1, an injector 1 according to the invention consists mainly of a body 2 on which a flap 3 is articulated pivotably and in which a slider or plunger 4 is arranged so that it is displaceable longitudinally. Thus, the injector consists solely of three simple components and is therefore simple to manufacture and handle.

Figure 2:
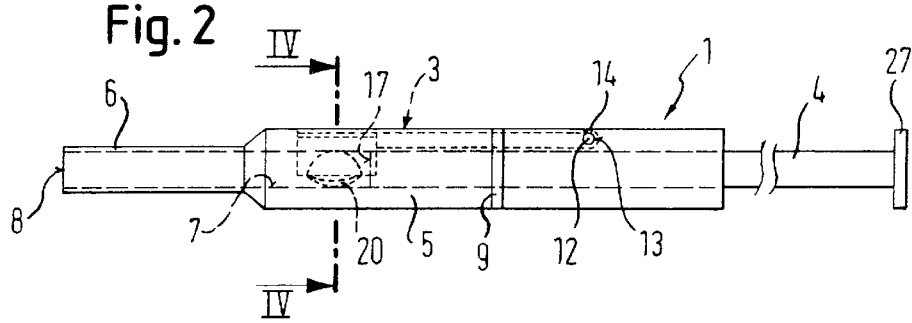
FIG. 2 shows a side view as in FIG. 1, with the flap pressed in and the lens folded as a result.

The one-piece body 2 consists of a thicker insertion and holding part 5 and a much thinner injection tube 6 and has a continuous transporting channel 7 with a constant cross-section. Both the body parts have a rectangular cross-section, as can be seen in FIG. 2. The front end-side of the injection tube 6 with the delivery opening 8 is embodied perpendicular to the longitudinal axis of the injector. A laterally extending grip plate 9 is secured on both sides of the body holding part 5 in the middle so that the injector can be handled like an injection syringe in particular when implanting the lens in the eye. In addition, these grip plates 9 serve to fix the injector in a transport container which will be described in greater detail below with reference to other figures.

As can be seen in FIGS. 1 to 4, the flap 3 consists of a lever 10 which on the underside of its front end exhibits a plate-shaped folding rib 11 which projects downwards. At its other end the pivoting lever 10 is mounted pivotably by means of laterally projecting stubs 12, which can also be seen in FIG. 3, on the upper side of the body holding part 2 in corresponding bearing bores 13. These bearing bores 13 are open towards the top through a snap-in slot 14 so that it is only necessary to press the stubs 12 into the bearing bores 13 through the snap-in slot 14 to assemble the flap 3 on the body 1. As is also clearly visible in FIG. 4, at its front end the flap 3 is provided with a wider thrust plate 15 on the underside of which the folding rib 11 is provided. As can also be seen in FIG. 1, the lens 20, which is still unfolded here, is held or arranged lying on a supporting surface 16 visible in FIG. 4 in the upper zone of the transporting channel 7, and is held by the underside of the folding rib 11 to prevent it from falling out unintentionally.

FIG. 2 shows the flap 3 pressed in, and it can be seen that in this state the lens 20 is folded in half and located entirely in the transporting channel 7. Here, the end side 17 of the plunger 4 is located behind the lens viewed in the direction of delivery, and when displaced longitudinally, can slide the lens forwards in the direction of the outlet opening 8 in the transporting channel 7.

Figure 5:
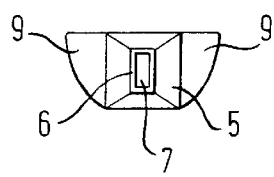
FIG. 5 shows an end elevation view according to the arrow V in FIG. 1.

FIG. 5 shows the rectangular embodiment of the injector body with the holding part 5, the injection tube 6 and the transporting channel 7. This figure also shows the two grip plates 9 which here are laterally rounded roughly in the shape of a quarter circle, matching the shape of the internal wall of the round transport container which will be described in greater detail further on. When a rectangular transport container is used, obviously the grip plates are also rectangular in shape.

Figure 3:
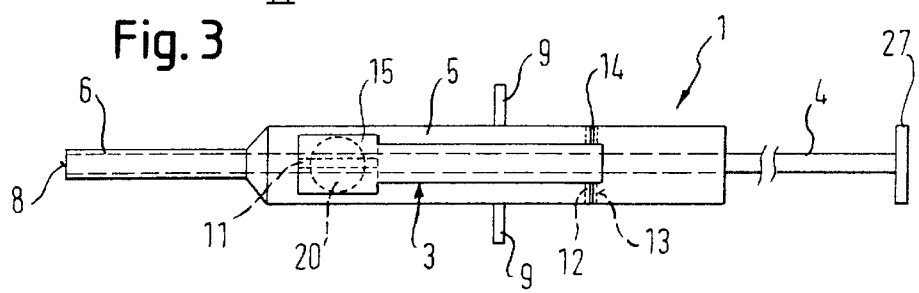
FIG. 3 shows a plan view of an injector according to FIGS. 1 and 2.
Figure 4:
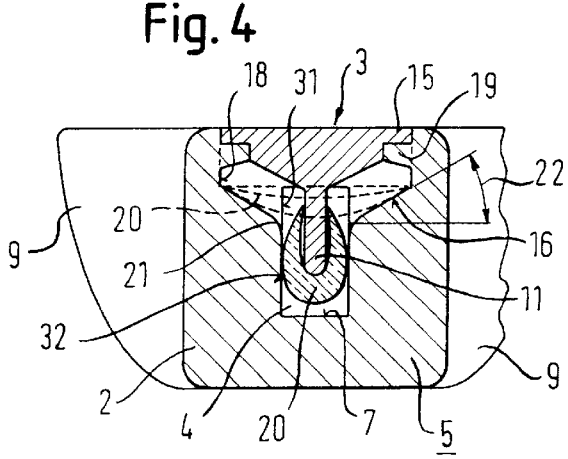
FIG. 4 shows a section IV—IV in FIG. 2, showing the relative arrangement of the individual components more clearly.

The rectangular shape of the body holding part 5 is clearly visible in FIG. 4, which provides a more detailed view of the situation of the flap in FIG. 3 when pressed in. This holding part 5 incorporates a rectangular slot which here—at least as far as its underside is concerned—is also part of the transporting channel 7 in which the slider 4 is introduced so that it is displaceable longitudinally. On the upper side of the holding part 5 there is an insertion opening 18 which in its length and width must at least exhibit the measurements of the lens 20 and can be round, as can be seen in FIGS. 3 and 9. In the embodiment illustrated in FIG. 4, a supporting strip 19 is provided on both sides of the insertion opening 18, on which the thrust plate 15 finally bears in its downward folding movement. At the same time, the strips 19 also serve to hold the lens roughly in position in that when the lenses are introduced past these strips, they snap into place on the supporting surface 16.

FIG. 4 also shows how the lens 20 is laid elastically around the folding rib 11 in the folded state and held inserted in the transporting channel 7. It can be seen that the supporting surface 16, which is divided into two parts by the transporting channel 7 which is open at the top in the form of a slot 31, runs via large radii into the side walls 32 of the transporting channel 7. In addition, the two parts of the supporting surface 16 are inclined to the horizontal at an angle 22 of approx. 30° and at the same time inclined towards the bottom of the transporting channel 7, making the folding and inserting movement of the lens 20 much easier. It can also be seen that through its supporting surface parts and the transporting channel slot the holding part 5 works like a mold and the flap 3 with the folding rib 11 works like a die of a bending or deep drawing tool.

FIGS. 6 to 14 show the three individual parts of an injector in a second embodiment individually in detail.

Thus, FIGS. 6 to 9 show an injector body, the holding part 5 of which is rectangular in form as in the previous example according to FIGS. 1 to 5, while its injection tube 6' and the transporting channel 7' exhibit a round cross-section. In addition, this view shows the arrangement of the bearing bores 13 and two indexing points, namely a first indexing point 24 for locking the flap with the folding rib lying on the unfolded lens, and a second indexing point 25 for locking the flap 3 in the position in which it is pressed in completely with the lens folded and inserted perpendicularly. In addition, it can be seen in particular in FIG. 6 that the front end side of the injection tube 6 is arranged with the delivery opening 8 at an oblique angle so that a front, injection tip 26 is formed which greatly facilitates introduction of this injector part through the small incision into the interior of the eye.

FIGS. 8 to 11 show that the pivoting lever 10 is wide and when pressed in is completely embedded in the surface of the holding part 5.

In addition, the indexing points 24 and 25 are visible in each case on both sides, however, the arrangement of indexing points on only one side can suffice.

FIGS. 10 and 11 show the embodiment of the flap, with a wide lever 10 and a narrow folding rib 11 which here is secured directly to the lever 10, without the thrust plate located over it. The arrangement of the mounting stubs 12, here in the form of projections, and the two indexing points 24 and 25, which are also provided in the form of projections on both sides of the lever, can also be seen here.

FIGS. 12 to 14 show a slider which in this embodiment has a round cross-section and on its outer side exhibits a thrust plate 27. On the upper side of the slider 4 there is a longitudinal groove 28 the width of which is selected according to the width of the folding rib so that the slider is still easily displaceable longitudinally even though the folding rib 11 is pressed into the transporting channel. In addition, on the front end side of the slider 4 there is an inward curve 29, following a quarter circle, matching the shape of the folded lens to be displaced. It can also be seen that three positioning devices are present on the slider, namely first positioning projections 33 for the retracted slider position, second positioning projections 34 for the advanced lens position, and a third end stop position 35 for the position in which the lens 20 is slid out of the injector completely.

FIG. 15 shows an injector 30 according to the invention to an approximate 1:1 scale in the second embodiment according to FIGS. 6 to 14. It can be seen that due to the extremely simple construction of the injector 30, which consists of only three parts, the extremely delicate design can be produced effortlessly in a very simple manner.

In addition, FIG. 16 shows a section XVI—XVI in FIG. 15, similar to the illustration in FIG. 4, with the flap 3 pressed in. Here, the lever 10 of the flap 3 is embodied as a continuous flat part on which the folding rib 11 is arranged on its lower front side. The underside of the lever 10 also serves as an insertion depth stop in co-operation with the supporting surface 16 for the unfolded lens 20. The transporting channel 7 is round and here the insertion opening debouches through a folding and insertion slot 31 with vertical walls 32 tangentially into the round transporting channel 7.

FIGS. 17 and 18 show a packaged injector 1, 30. An injector 1, 30 according to the invention is inserted in a transport container 40 which in turn is placed in a packaging carton 41 in which a packing slip 42 is also packed.

It can be seen that the transport container 40 consists of a sleeve 39 which is closed by a cover 38. Here, a sleeve 39 with a round cross-section is provided. However, it can also exhibit a rectangular cross-section.

Arranged in the interior of the sleeve 39 there are two transversely spaced plates 43 which are spaced in relation to one another so that the holding part 5 of the body 2 can easily be slid in between them. The holding plates 43 serve as a longitudinal insertion stop for the injector through its grip plates 9 in the direction of insertion. On their free upper side the holding plates 43 have hooks 44 which point in the direction of insertion and grip around the upper side of the grip plates 9 and thus hold the injector lying on the wall of the sleeve 39. In addition, the cover 38 exhibits a projection 37 which runs axially and extends to the rearward end side of the body holding part of the injector, so that the body 2 is clamped securely between the holding plates 43 and the projection 37 after the cover 38 is closed. Thus, unintentional insertion of the slider 4 and ejection of the unfolded lens 20 from the injector can be avoided even if the transport container 40 is handled incorrectly and possibly dropped.

However, a spacer clip not shown in the drawing can also be used in place of the projection 37 provided on the cover 38. This clip has a length equal to the spacing between the rearward end face of the holding part and the thrust plate of the slider in the retracted first slider position. It can be a slotted tube which can easily be slid up and down transversely on the sliding rod. In addition, then the outer end face of the slider thrust plate is supported on the inside of the cover, which is favourable when this inside is lined with a very soft material such as foam.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. An injector for implanting/inserting a temporarily folded intraocular lens, with which the folded lens can be inserted into a capsula of a lens of an eye through an opening incision of about 3 mm in the eye, the injector comprising:

a one-piece body having a thicker insertion and holding part and a thinner injection tube on an injection side and a continuous axial opening with a constant cross-section as a transporting channel;

a slider arranged so as to be displaceable axially in the transporting channel;

an insertion opening in the insertion and holding part transversely and symmetrically in relation to an axis of the transporting channel, the insertion opening acting as an insertion channel for the lens and communicates with the continuous transporting opening, the insertion and holding part having a supporting surface at the insertion opening on which the unfolded lens lies flat for transport, the supporting surface being arranged inside the holding part offset upwards in a direction of insertion in relation to the axis of the transporting channel, and runs through an insertion slot, having a width equal to a width of the transporting channel, into the transporting channel; and a folding rib extending longitudinally and centrally in relation to the lens, the folding rib being plate-shaped and extends radially so as to be pressable radially into the transporting channel through the insertion opening whereby the lens is inserted completely into the transporting channel folded around the folding rib.

2. An injector according to claim 1, wherein the injector body has a rectangular cross-section and the transporting channel has a rectangular cross-section.

3. An injector according to claim 2, wherein the cross-section of the transporting channel is configured to permit transport of the folded lens with the folding rib pressed in the transporting channel.

4. An injector according to claim 1, wherein the slider is a rod with a uniform cross-section, the rod having an upper side with a groove into which the pressed in folding rib extends during displacement of the slider, the slider having an end side with an inward curve roughly following a quarter cylinder and matching an edge of the folded lens.

5. An injector according to claim 4, and further comprising three positioning devices provided on the slider and the body in a sliding direction of the slider so as to position the slider in a first retracted slider position with the lens insertion opening exposed, a second position with the folded lens slid forward close to a front delivery opening, and a third end stop position in which the lens is slid completely out of the injector.

6. An injector according to claim 1, wherein the supporting surface for the unfolded lens includes two partial surfaces which are separated by the insertion slot, are inclined inwards toward the transporting channel at an angle of about 20° to horizontal, and run via radii into side walls of the transporting channel and the insertion slot.

7. An injector according to claim 6, and further comprising supporting strips for stop strips of the folding rib provided on both longitudinal sides of the insertion opening above the supporting surfaces.

8. An injector according to claim 1, and further comprising a pivotable lever articulated at a rear end pivotably on an upper side of the body, the folding rib being provided at a front end of the pivoting lever.

9. An injector according to claim 8, wherein indexing devices are provided on the lever of the folding rib, which is pivotable through about 180°, and detent means are provided on the body so that the indexing devices and the detent means interact to determine the angular position of the lever when lying on and holding the unfolded lens and when pressed in and holding the folded lens.

10. An injector according to claim 9, wherein the lever is widened at a point level with the folding rib to roughly a width of the body so as to form a thrust plate which is supported on one of the supporting surface and the supporting strips when pressed in and simultaneously support the folding rib radially.

11. An injector according to claim 8, wherein the body, the lever and the slider are made of transparent plastic and are configured so that they are connected together by sliding and pressing into one another, and further comprising one of snap projections and locking joints arranged to hold the body, the lever and the slider together.

12. An injector according to claim 11, and further comprising a grip plate provided on both sides at a midsection of the body holding part so as to extend transversely from the body holding part.

13. An injector according to claim 11, wherein the injector body has a round cross-section with a round transporting channel and a round slider rod, and the radial insertion and folding slot between the lens supporting surface and the transporting channel has longitudinal walls that run tangentially to the transporting channel walls.

* * * * *